(12) United States Patent
Antkowiak et al.

(10) Patent No.: US 8,736,935 B2
(45) Date of Patent: May 27, 2014

(54) OPTICAL DEFLECTION DEVICE FOR SCANNING, OPHTHALMOLOGIC MEASUREMENT AND THERAPY SYSTEM

(75) Inventors: Gerard Antkowiak, Jena (DE); Thomas Pabst, Stadtroda (DE); Ralf Ebersbach, Schmölln (DE); Heino Weigand, Jena (DE); Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 730 days.

(21) Appl. No.: 12/886,145

(22) Filed: Sep. 20, 2010

(65) Prior Publication Data

US 2011/0069366 A1 Mar. 24, 2011

(30) Foreign Application Priority Data

Sep. 18, 2009 (DE) .................. 10 2009 041 995

(51) Int. Cl.
*G02B 26/08* (2006.01)
(52) U.S. Cl.
USPC .................. 359/200.7; 359/202.1
(58) Field of Classification Search
USPC .............. 359/199.3, 200.7, 202.1
See application file for complete search history.

(56) References Cited

U.S. PATENT DOCUMENTS

| | | | | |
|---|---|---|---|---|
| 5,629,790 | A * | 5/1997 | Neukermans et al. | 359/198.1 |
| 5,999,302 | A | 12/1999 | Sweeney et al. | |
| 6,069,725 | A * | 5/2000 | Melville | 359/212.1 |
| 6,086,209 | A | 7/2000 | Miyahara et al. | |
| 6,726,325 | B2 | 4/2004 | Xie et al. | |
| 7,050,208 | B2 | 5/2006 | Overbeck | |
| 7,064,876 | B2 * | 6/2006 | Cannon et al. | 359/204.1 |
| 7,126,744 | B2 * | 10/2006 | Turner et al. | 359/298 |
| 7,312,911 | B2 * | 12/2007 | Tan et al. | 359/204.3 |
| 7,365,856 | B2 | 4/2008 | Everett et al. | |
| 7,388,672 | B2 | 6/2008 | Zhou et al. | |
| 8,144,380 | B2 * | 3/2012 | Takeuchi | 359/199.3 |

(Continued)

FOREIGN PATENT DOCUMENTS

| | | |
|---|---|---|
| DE | 29 51 593 A1 | 7/1981 |
| DE | 38 33 260 A1 | 6/1989 |

(Continued)

OTHER PUBLICATIONS

Leitgeb, R., et al., "Performance of fourier domain vs. time domain optical coherence tomography," *Optics Express*, vol. 11, No. 8, Apr. 23, 2003, pp. 889-894.

(Continued)

*Primary Examiner* — Frank Font
(74) *Attorney, Agent, or Firm* — Patterson Thuente Pedersen, P.A.

(57) ABSTRACT

An optical deflection unit for targeted radiation, e.g., produced by laser or superluminescent diodes, in scanning, ophthalmological measuring and therapy systems, comprises a deflection mirror, a position sensor and a control unit, which form a control circuit for minimizing the deviation of the actual positions, detected by the position sensor, from the desired positions of the deflection mirror, whereby the optical deflection unit comprises a deflection mirror, oscillatingly movable by means of non-contacting electromagnetic drives around at least one rotation axis, and which is positioned in the direction of the, at least, one rotation axis between at least two bearings. The optical deflection unit is designed may also be used for beam guidance in high and ultrahigh vacuum installations, such as UV and EUV exposure installations for semiconductor lithography.

25 Claims, 3 Drawing Sheets

(56) References Cited

U.S. PATENT DOCUMENTS

| | | | |
|---|---|---|---|
| 8,154,784 B2* | 4/2012 | Sasaki | 359/213.1 |
| 2003/0197910 A1 | 10/2003 | Witt et al. | |
| 2005/0018137 A1 | 1/2005 | Barth et al. | |
| 2005/0030475 A1 | 2/2005 | Zhou et al. | |
| 2006/0228011 A1 | 10/2006 | Everett et al. | |
| 2007/0053044 A1* | 3/2007 | Kawakami et al. | 359/223 |
| 2007/0242329 A1* | 10/2007 | Ballegaard et al. | 359/201 |
| 2007/0291277 A1 | 12/2007 | Everett et al. | |
| 2008/0231808 A1 | 9/2008 | Van de Velde | |
| 2008/0284981 A1 | 11/2008 | Fercher | |
| 2009/0051997 A1 | 2/2009 | Maeno et al. | |
| 2009/0073538 A1 | 3/2009 | Simon et al. | |
| 2009/0128878 A1* | 5/2009 | Jun et al. | 359/199.3 |
| 2010/0284021 A1 | 11/2010 | Hacker | |

FOREIGN PATENT DOCUMENTS

| | | |
|---|---|---|
| DE | 196 35 998 C1 | 4/1998 |
| DE | 10 2007 046 507 A1 | 4/2009 |
| GB | 927042 | 5/1963 |
| GB | 2 317 227 A | 3/1998 |
| WO | WO 2006/015717 A1 | 2/2006 |
| WO | WO 2006/077107 A1 | 7/2006 |

OTHER PUBLICATIONS

Yun, S.H., et al., "Motion artifacts in optical coherence tomography with frequency-domain ranging," *Optics Express*, vol. 12, No. 13, Jun. 28, 2004, pp. 2977-2998.

* cited by examiner

OPTICAL DEFLECTION DEVICE FOR SCANNING, OPHTHALMOLOGIC MEASUREMENT AND THERAPY SYSTEM

PRIORITY CLAIM

This application claims priority to German Patent Application No. 10 2009 041 995.0 filed on Sep. 18, 2009, said application is incorporated herein by reference in it's entirety.

FIELD OF THE INVENTION

The invention relates to an optical deflection unit for targeted radiation in scanning, ophthalmological measuring and therapy systems and other applications.

BACKGROUND OF THE INVENTION

Optical deflection units for targeted radiation in scanning, ophthalmological measuring and therapy systems and other applications, produce radiation, e.g., through laser or superluminescent diodes, utilized for targeted illumination of eye structures in order to gain information from the backscattered light portions in the ophthalmological measuring devices or to achieve treatment effects in the eye tissue with therapy systems. From DE 196 35 998 C1, the combination of such a measuring and therapy device using targeted optical radiation is known.

Examples of ophthalmological measuring devices are biometric systems for the determination of sizes, distances, and/or geometric relations of eye structures. Such measurement results are required for the adjustment of implants, such as intraocular lenses after cataract operations, but are also suited for the diagnosis of certain clinical pictures, e.g., narrow-angle glaucoma.

Therapy systems using specifically applied, targeted radiation are, for example, laser systems for follow-up treatment of cataract diseases or for coagulation of retinal areas in case of retinal detachments.

For scanning measuring as well as therapy devices, one- or two-dimensional deflection patterns are most commonly used, which are to be realized by the deflection unit. Examples are laser retina treatments, whereby adjusted dot patterns for different retinal areas are frequently used in order to achieve optimal therapy effects at minimized patient impairment. This also applies to imaging, ophthalmological measuring systems such as optical coherence tomographs (OCT) or scanning laser ophthalmoscopes (SLO).

Such imaging, ophthalmological measuring systems are primarily used to produce two-dimensional images, sectional images, and volume scans of various areas of the eye and to evaluate with regard to visual impressions, sizes, and distances of certain eye structures. For example, solutions are known from prior art, which thereto utilize optically based scan systems.

Measurements continue to be performed with biometric, ophthalmological measuring systems, whereby a measurement beam is positioned but otherwise not deflected. An example thereto is the sectional measurement on the eye, according to US 2005/018137 A1. However, if position and curvature of boundary layers and structures, which are not only located on the optical axis of the eye, are to be detected biometrically, two-dimensional measurements are also used (according to WO 2006/015717 A1).

A first group of the imaging, ophthalmological measuring systems are hereto tomography systems, which, e.g., are based on the so-called OCT (optical coherence tomography) method, whereby short coherent light with the help of an interferometer is employed for distance measurement of reflective and scattering materials (US 2007/0291277 A1). Through depth scans, the optical coherence tomography on the human eye delivers measurable signal responses due to the scattering at index of refraction changes, particularly at optical boundaries. Known variations are the time-domain OCT (TD-OCT) and Fourier-domain OCT (FD-OCT) with its versions, which are based on the application of spectrometers (SD-OCT) of spectrally tunable light sources (SS-OCT). Thereto, see Leitgeb et al. "Performance of Fourier domain vs. time domain optical coherence tomography," Opt. Express Vol. 11, 889 (2003).

A second group comprises ophthalmoscopes, particularly scanning laser ophthalmoscopes (SLO), which, in addition to the OCT-based tomography systems, also represent known and important tools for diagnosis and therapy in ophthalmology (US 2005/030475 A1).

In order to obtain the images required for the diagnosis in the form of two-dimensional images, sectional images, and volume scans, scans, in addition to A-scans (individual depth profiles), are required transversally in a first (B-scans) and a second direction (volume scans and scans at a constant reference plane, so-called C-scans).

Thereby it is very important to record those scans very quickly since the available attention span of a patient (with barely 2 sec.) is very limited. Furthermore, according to Yun et al. "Motion artifacts in optical coherence tomography with frequency-domain ranging," Opt. Express, Vol 12, 2977 (2004), motion artifacts can, as a result, be limited and corrected in accordance with the solution in WO 2006/077107 A1.

Therefore, very quick deflection systems for the measurement beams must be deployed in such imaging systems. At the same time, said deflection systems must be able to render a predetermined scan pattern very accurately, linearly, and very reproducibly, ensuring that the emerging sectional images and volume scans exhibit no distortions which would make the evaluation of the structures needlessly difficult.

Said great challenges to the deflection devices regarding speed and control accuracy are, e.g., further enhanced when so-called tracking systems, already widely used in ophthalmology, are utilized which detect, register and/or actively compensate the eye movements during the course of the measurements. Such tracking systems are described, for example, in U.S. Pat. No. 6,726,325 B2; U.S. Pat. No. 7,365,856 B2; and US 2006/228011 A1.

In order to meet these requirements regarding speed and control accuracy, stably rotating polygon mirrors for realizing close to linear sawtooth or triangular scans, or galvanometer mirrors within closed control loops are used according to prior art.

Polygon mirrors are able to scan very quickly and stably but are limited to a defined deflection pattern in a defined direction. Additionally, they have distortion and are expensive.

By contrast, galvanometer mirrors are able to realize different scan patterns but also require great electronic control efforts (closed-loop galvanometers with position feedback sensors) in order to reproduce a predetermined deflection pattern with accuracy, linearity, and reproducibility acceptable for imaging.

Therefore, combinations of both systems are also frequently employed as scan unit in ophthalmological devices, whereby a quickly rotating polygon mirror produces a fixed deflection pattern in a deflection direction and a galvanometer mirror realizes a possibly deviating deflection pattern in a second, slower deflection direction.

The most frequently utilized deflection systems in ophthalmological scanners, as described in US 2008/231808 A1, exhibit modern galvanometer scanners with an optical position detection system, which, via an electronic control unit, allows for active control of the mirror movement, including the damping of interferences (U.S. Pat. No. 5,999,302 A).

With the polygon mirror, a stabilization of the rotation frequency is essentially realized. Major disadvantages of galvanometer scanners and polygon mirrors are the limitation of one rotation axis each as well as wear and tear and required lubrication of the bearings.

The solutions for deflection systems for scanning measurement value logging, which are known in accordance with prior art and described herein, particularly fast volume scans, are "oversized" for the measuring and therapy tasks to be solved and have the additional disadvantage of being very elaborate and expensive.

Aside from galvanometer and polygon scanners, additional optical systems for deflection of light beams are known, according to prior art, which do not apply to the field of ophthalmology.

Examples of acousto-optical and electro-optical scanners are known from U.S. Pat. No. 7,050,208 B2 and US 2009/0073538 A1. Even though they are suited as optical deflection systems without mechanical moment of inertia for very fast deflections, they also require great efforts regarding control since very exact electrical high voltages or high-frequency signals are generated.

DE 38 33 260 A1 describes a light deflection device, whereby a mirror is moved as quickly and precisely as possible around a rotation axis located in the mirror plane. Thereto, the suspension of the mirror is disclosed as flexural pivot, the spring elements of which consist of piezoelectric material. Through applying voltage to the spring elements, the mirror can be moved with this mechanism at low energy and with high motion frequency due to the piezoelectric material properties. Piezoelectric actuators also exhibit the disadvantage of generating very exact high voltages. Furthermore, it is known that this type of control with piezoelectric actuators leads to premature material fatigue due to small microcracks.

A support for a scanning mirror is disclosed in DE 29 51 593 A1. Thereby, the scanning mirror oscillates with natural resonance around an axis in the mirror plane. In order to facilitate a larger rotation angle of the oscillation at the same oscillation frequency, the support is formed from two aligned connected flexural pivots. Hereto it is disadvantageous that deflections can only be realized at certain deflection frequencies which does not allow for high flexibility regarding the deflection pattern generation.

The invention herein is based on the task of developing an optical deflection unit for ophthalmological diagnosis and therapy systems, whereby the known disadvantages from prior art are remedied and which is significantly more cost-effective and less elaborate. Furthermore, the optical deflection unit shall be characterized by simplicity, durability, robustness, improved reproducibility as well as decreased aging and temperature effects. In addition, the optical deflection unit should be capable of realizing relatively large deflections of ±10° in two deflection dimensions with a compact design.

SUMMARY OF THE INVENTION

An optical deflection unit for ophthalmological diagnosis and therapy devices comprises a deflection mirror, movable by means of non-contacting electromagnetic drives and oscillating around at least one rotation axis, and positioned between at least two bearings. The unit further comprises a position sensor for the deflection mirror and a control unit, which form a control circuit for minimizing the deviation of the actual positions, detected by the position sensor, from the desired positions of the deflection mirror.

Even though the optical deflection unit, according to the invention, is particularly suited for ophthalmological diagnosis systems, it can also find use in other ophthalmological devices and in other applications.

Particularly, the deflection unit is suited for application in diagnostic devices which are based on an interferometric measurement arrangement, consisting of a light source for the realization of the measurement tasks, a two-beam interferometer (U.S. Pat. No. 7,388,672 B2; DE 10 2007 046 507 A1), a signal detection as well as a central control unit with pattern generation and an output unit as well as a deflection mirror of the deflection unit, positioned in the measurement arm of the two-beam interferometer. A particularly preferred embodiment is an interferometric measurement arrangement for performing OCT measurements in accordance with the swept-source OCT principle (SS-OCT), using a spectrally tunable laser light source and balanced detection.

Even though the optical deflection unit is designed for ophthalmological applications, particularly for biometric systems, it can, as a lubrication-free version, also be used for beam guidance in high and ultrahigh vacuum installations, such as (UV and EUV) exposure installations for semiconductor lithography. Hereby, it is also favorable that the actuation is effected via stationary electromagnets, whereby the heat dissipation in the vacuum is significantly simpler than with systems moving alongside.

More particularly, an optical deflection unit beam guidance in high and ultrahigh vacuum installations, such as UV and EUV exposure installations for semiconductor lithography comprising a deflection mirror, oscillatingly movable through non-contacting electromagnetic drives around at least one rotation axis, and which is arranged between at least two bearings in the direction of the at least one rotation axis, a position sensor, and a control unit, the deflection mirror, the position sensor, and the control unit forming a control circuit for minimizing the deviation of the actual positions, detected by the position sensor, from the desired positions of the deflection mirror.

BRIEF DESCRIPTION OF THE DRAWINGS

In the following, the invention will be further described by means of example embodiments.

DETAILED DESCRIPTION

Figure 1:
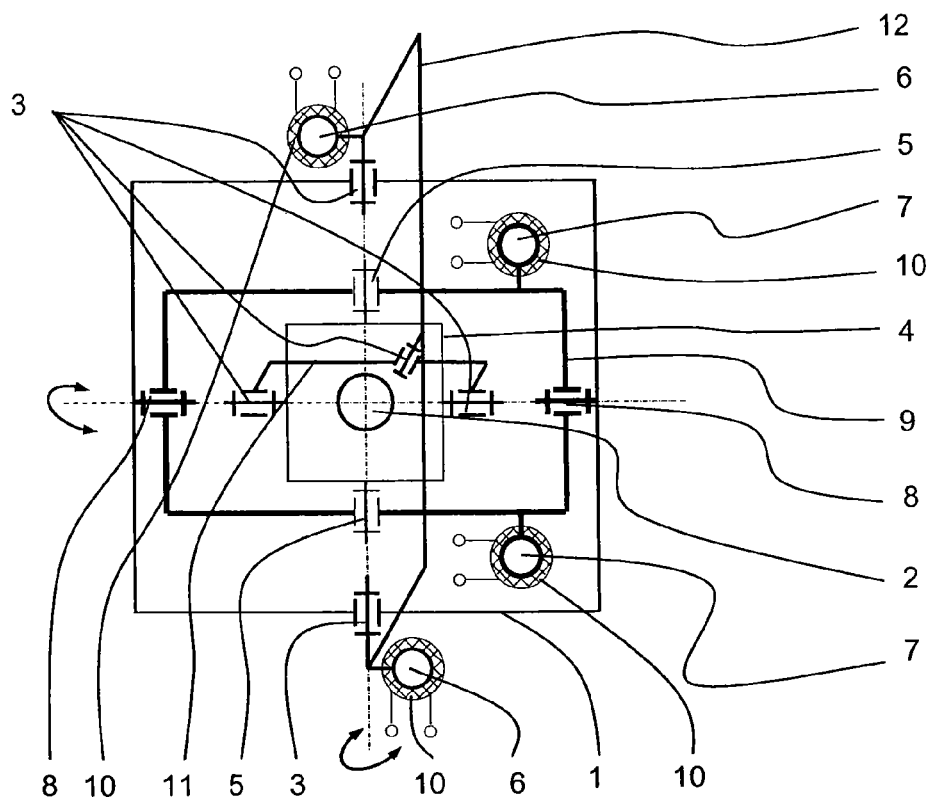
FIG. 1 is a schematic drawing of a mechanically decoupled deflection unit with two movable frames.

The deflection unit for scanning, ophthalmological measuring and therapy systems, according to an embodiment of the invention, exhibits a deflection mirror, a position sensor and a control unit, which form a control circuit for minimizing the deviation of the actual positions, detected by the position sensor, from the desired positions of the deflection mirror. Hereby, the optical deflection unit comprises a deflection mirror, movable by means of non-contacting electromagnetic drives and oscillating around at least one rotation axis, and which is positioned in the direction of the, at least, one rotation axis between at least two bearings.

The deflection unit, activated through non-contacting electromagnetic drives, functions hereby as non-resonant scanner. Via the closed control circuit, which comprises a control for the realization of the scan patterns transmitted from the pattern generation, and a position sensor for the detection of the actual positions of the deflection mirror of the deflection mirror unit, the realization of the scan pattern as well as the compensation of internal and external interferences may be effected. Thereto, a continuous comparison of nominal and actual values takes place inside the closed control circuit in order to minimize the difference between nominal and actual.

It is known to experts in the art that the electronic control circuits must be designed in such a way that electronic noise within the control circuit only causes acceptable interferences for the pattern generation. It is also known to the expert that mechanical interactions may occur between the mechanical components, which realize the various deflection directions, and that the mechanical components with regard to their rigidity and geometry must be designed in such a way that unwanted mechanical resonances are minimized.

An aspect of the optical deflection unit, according to an embodiment of the invention, is that in addition to the targeted radiation utilized by the diagnosis or therapy device an additional light beam is used, which is also deflected during the deflection of the deflection mirror, and the position change of which is position-sensitively determined by a sensor. As a result, by means of the additional light beam, in particular, a position measurement can be effected directly on the optical surface, which also deflects the targeted radiation, which is to be utilized in the diagnosis or therapy system. Thereby, particularly measurement errors can be avoided, which would otherwise occur during the recording of the positional information on locations other than the deflecting surface. Such errors would, for example, occur through twisting or sagging of the dynamically moved mechanical links.

Particular embodiments are described below.

In a first embodiment (not shown), the optical deflection unit comprises a housing with a frame which holds the deflection mirror and which is rotatingly movable around a rotation axis. Thereby, the movable frame is secured to the housing via two bearings and exhibits permanent magnets which are facing drives in the form of electromagnets, preferably air-cored coils or plunger coils, inside the housing.

Air-cored coils or plunger coils are advantageous since other core materials may intensify the magnetic force but also produce offset forces which have to be taken into consideration with regard to the control.

According to an embodiment of the invention, the movable frames for holding the permanent magnets are, preferably, made of non-magnetizable or only slightly magnetizable materials, such as aluminum, magnesium or non-magnetizable steel. In order to avoid undesired dynamic effects between the components, non-magnetizable frame material is additionally advantageous for cardan suspensions. However, with careful magnetic decoupling, the use of magnetic frame materials, which allow for a closure of the magnetic flow and therefore improvement the dynamic effect, is also possible.

While said first embodiment represents a one-dimensional and/or single-axis deflection unit, a second embodiment provides a deflection unit, which allows for a two-dimensional deflection through additions to the scanner described in the first embodiment.

Thereby, the deflection unit described in the second embodiment (also not shown) also comprises a housing with a frame which holds the deflection mirror and which is oscillatingly movable around a rotation axis. The movable frame is also secured to the housing via two bearings and exhibits permanent magnets which are facing drives in the form of electromagnets, preferably air-cored coils or plunger coils, inside the housing. Contrary to the first embodiment, the frame, which holds the deflection mirror and which is oscillatingly movable around a rotation axis and which is positioned inside the housing, is further pivoted around an additional rotation axis, whereby the two rotation axes lie orthogonally to one another. This results not only in the option of realizing one-dimensional but also ring-shaped, star-shaped, and two-dimensional scans, which is suitable for many tasks in ophthalmological diagnostics and therapy.

This can also be achieved through positioning a rotating optical unit for beam rotation downstream of the first embodiment. For the realization of such tasks dove prisms or other prism-based mirror assemblies are utilized, according to prior art. Such assemblies for beam rotation are, e.g., described in GB 927 042.

Therein, a reflective embodiment is described for avoiding color aberrations which would otherwise occur with refractive devices. In a preferred embodiment, the rotation axis of the scanner and the rotation axis of the rotation unit intersect.

In a third embodiment, the deflection unit comprises a housing with two movable frames, the principle structure of which is shown in FIG. 1.

Hereby, the optical deflection unit comprises a housing 1 with two movable frames 4 and 9, whereby the inner of the two movable frames 4 holds the deflection mirror 2, exhibits permanent magnets 6 and is secured via two bearings 5 in the outer movable frame 9, which itself also exhibits permanent magnets 7 and is secured via two bearings 8 within the housing 1, and whereby inside the housing 1 non-contacting electromagnetic drives in the form of electromagnets 10 are positioned, which are facing the permanent magnets. Thereby, the two rotation axes of the oscillatingly moving frames 4 and 9 are, preferably, arranged orthogonally to one another.

As in the previous embodiments, the oscillating motion of the deflection mirror 2 is effected via non-contacting, electromagnetic drives in the form of permanent magnets 6 and 7 positioned on the movable frames, as well as electromagnets 10, preferably air-coned coils or plunger coils, arranged inside the housing 1, whereby the permanent magnets 6, 7 and the electromagnets 10 are facing each other respectively.

This third embodiment allows, particularly, for constant directions of the dynamic effects between permanent magnets 6, 7 and electromagnets 10 since an ideal mechanical decoupling between the two rotation axes via the brackets 11 and 12 as well as the bearings 3 was achieved. This prevents, particularly, that the dynamic effects between permanent magnets 6, 7 and electromagnets 10 for one rotation axis also affect the other rotation axis. This mechanically largely decoupled embodiment is particularly suited for mirror tilting of 5° and beyond.

Figure 2:
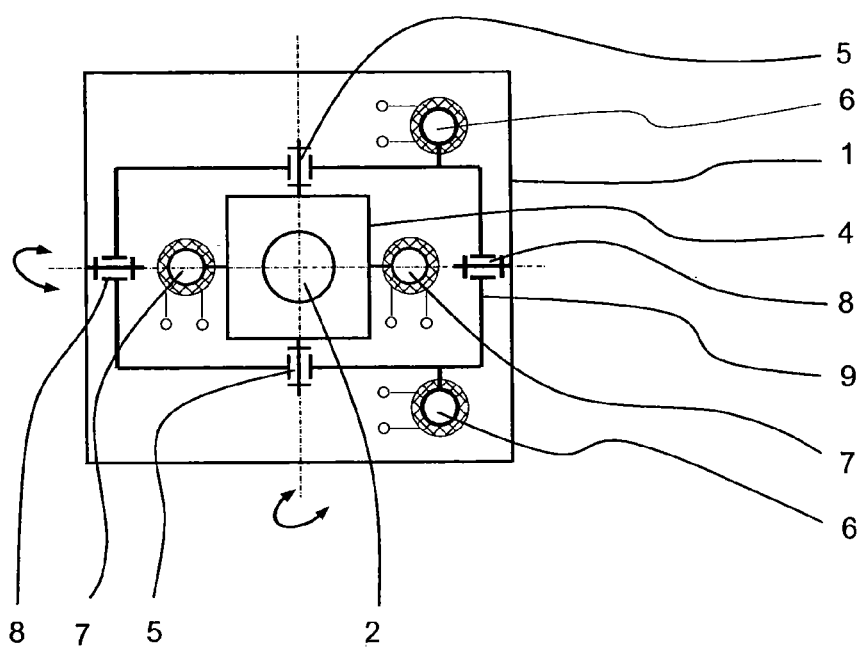
FIG. 2 is a schematic drawing of a deflection unit, which is not mechanically decoupled, with two movable frames.

In a fourth embodiment, the deflection unit also comprises a housing with two movable frames and is shown as principle structure in FIG. 2. Once again, the optical deflection unit comprises a housing 1 with two movable frames 4 and 9, whereby the inner of the two movable frames 4 holds the deflection mirror 2, exhibits permanent magnets 6 and is secured via two bearings 5 in the outer movable frame 9, which itself also exhibits permanent magnets 7 and is secured via two bearings 8 within the housing 1, and whereby inside the housing 1 non-contacting electromagnetic drives in the form of electromagnets 10 are positioned, which are facing the permanent magnets. Thereby, the two rotation axes of the oscillatingly moving frames 4 and 9 are, preferably, arranged orthogonally to one another.

In this fourth embodiment, a complete mechanical decoupling is not achieved. Since the dynamic effects between permanent magnets 6, 7 and electromagnets 10 for one rotation axis slightly affect the other rotation axis, this has to be taken into consideration for the control of the electromagnets 10, if necessary. Thereto, e.g., a control via a two-dimensional characteristic field would be suitable. The embodiment described hereto is, compared to the previously described mechanically decoupled variation, particularly suited for mirror tilting of up to 5°. Hereby, air-coned coils and plunger coils are equally suited as electromagnets 10.

Figure 3A:
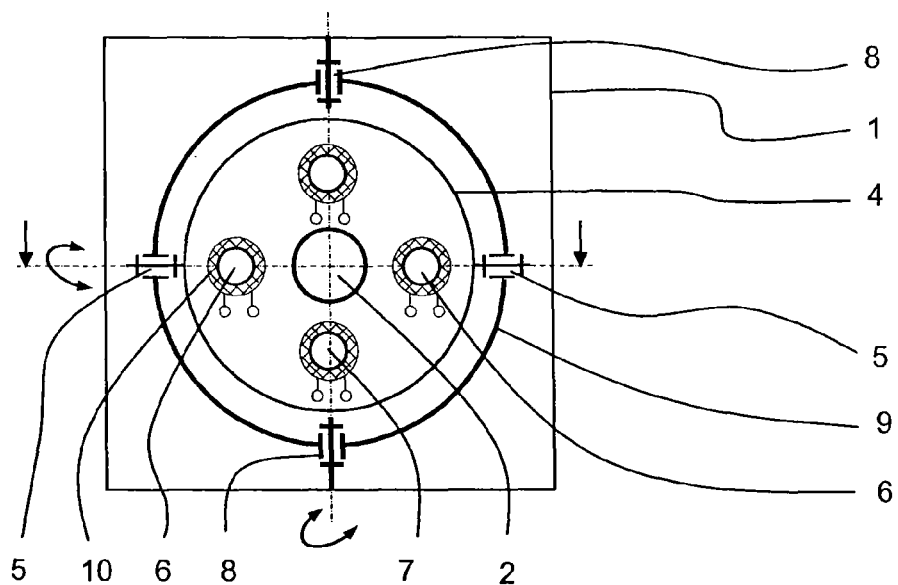
FIG. 3a is a schematic drawing from below of a deflection unit, which is not mechanically decoupled, with two movable frames.
Figure 3B:
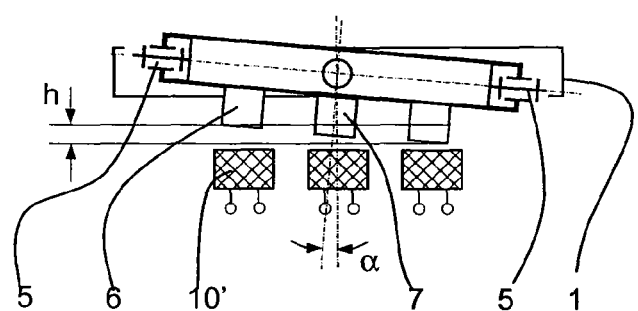
FIG. 3b is a side schematic view of the deflection unit, according to FIG. 3a, with electromagnets in the form of air-cored coils.
Figure 3C:
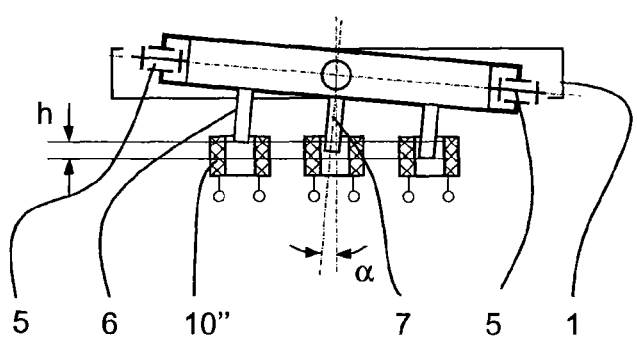
FIG. 3c is a side view of the deflection unit, according to FIG. 3a, with electromagnets in the form of plunger coils.
Figure 4:
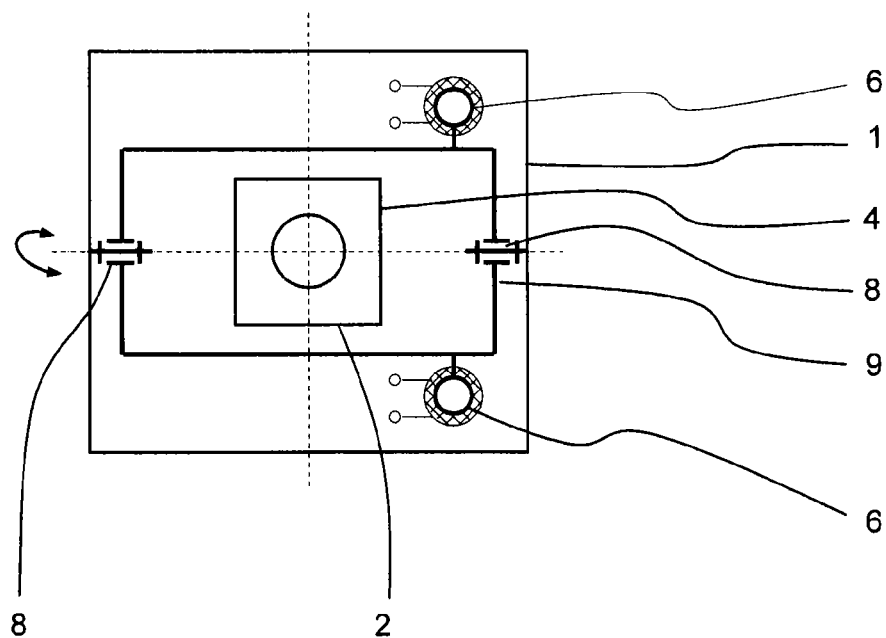
FIG. 4 is a schematic drawing of a deflection unit according to an example embodiment of the invention.
Figure 5:
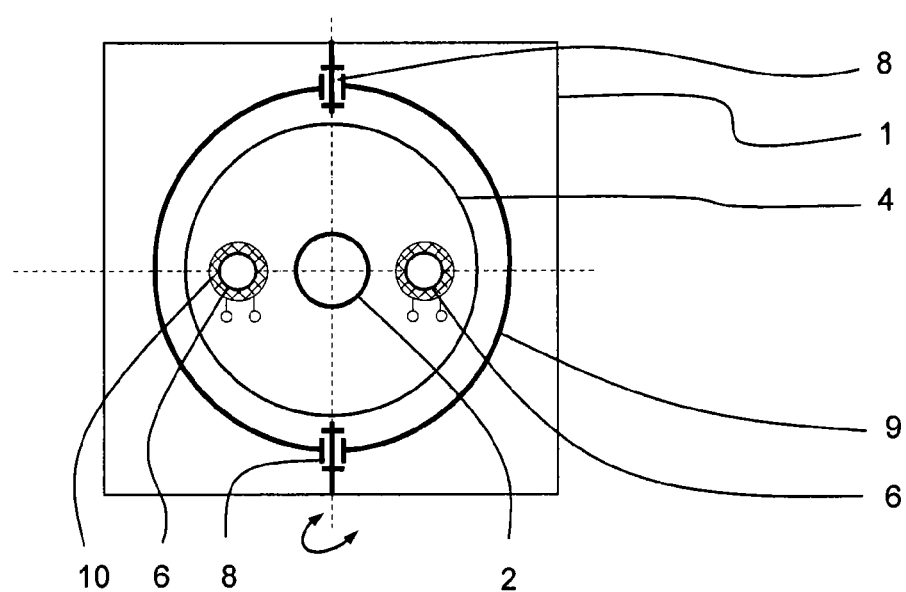
FIG. 5 is a schematic drawing from below of a deflection unit according to an example embodiment of the invention.

Thereto, FIGS. 3 to 3c show detailed views of a not mechanically decoupled deflection unit with two movable frames 4 and 9. While FIG. 3a shows the deflection unit from below, FIG. 3b shows the side view of the deflection unit with electromagnets 10 in the form of air-coned coils 10' and FIG. 3c the side view of the deflection unit with electromagnets 10 in the form of plunger coils 10".

Even though air-coned coils and plunger coils are equally suitable for this variation, plunger coils, whereby the permanent magnets are always at least partially inside the electromagnets, are advantageous since a more even dynamic effect along the translational motion paths can be achieved.

The impact of the dynamic effect between permanent magnets and electromagnets for one rotation axis onto the other rotation axis shall be briefly explained for the use of plunger coils. As a result of the control of the electromagnets for the oscillating movement of the deflection mirror around a first rotation axis, the permanent magnets of the frame to be moved, which face said electromagnets, are moved through a change of their penetration depth in the air-coned coils, whereby the movement effects the height adjustment h as well as a tilting of the permanent magnets around the angle α. By contrast, the permanent magnets (the electromagnets of which are not controlled) responsible for the second rotation axis are only tilted once which barely affects the driving forces (magnetic fields) of the first rotation axis.

A first preferred embodiment with regard to the deflection mirror unit can be seen in the detachable connection between the deflection mirror and movable frame, for example, through screw connection. This not only allows for the replacement of the deflection mirror but also the removal and reinstallation for cleaning purposes. Adhesion, for example, represents another variation for the attachment of the deflection mirror.

It is furthermore advantageous that the movable frames as well as the arrangement of the permanent magnets are executed symmetrically to the rotation axes, whereby the permanent magnets are, preferably, arranged in pairs on the rotation axis. This has the advantage that the centers of gravity of the frames are located on the rotation axes, resulting in a more stable, horizontal rest position of the deflection mirror. In addition, the forces to be applied for the oscillating movement of the frames and the mirror are also symmetrical, which significantly simplifies the control.

An additional significant simplification for the realization of the scan pattern and the compensation of internal and external interferences can be achieved in such a way that the frame, which holds the deflection mirror, is secured in the housing in such a way that the rotation axis (axes) lie(s) within the mirror plane.

In a further advantageous embodiment, lubrication-free flexural pivots of pretensioned hybrid ball bearings, which utilize ceramic balls, are used as bearings for the movable frames. Of course, different bearings for each frame are also conceivable. The flexural pivots utilized in accordance with the invention have the advantage of being free of dynamic and rolling friction as well as low in wear and tear and require no lubrication and/or use of special bearing materials. Flexural pivots exhibit high durability and can also be used as return springs. With the use of flexural pivots it must be made sure that they can only be stressed within predetermined displacement limits in order to remain fatigue-proof. Hence, the cardan suspension does not allow for random rotations.

The utilized hybrid ball bearings are free of dynamic friction and rolling friction as well as low in wear and tear and, due to pretensioning, have the advantage of very little play which significantly increases the stability of the overall construction, particularly with the use of two movable frames.

In the previously described advantageous embodiments of the deflection mirror unit, the control is effected via a closed control circuit, which comprises a control for the realization of the scan pattern, transmitted by the pattern generation, and a position sensor for the detection of the actual positions of the deflection mirror of the deflection mirror unit. Thereby, the function of the closed control circuit is the realization of the scan pattern as well as compensation of internal and external interferences. Thereto, an active control through a continuous comparison of nominal and actual values of the displacement of the deflection mirror for both deflection directions takes place, whereby the difference (nominal-actual) is minimized.

Hereby, internal interferences, such as resonances and the like, as well as external interferences are compensated during operation, which might occur, e.g., due to vibrations, jolts, or microphonics effects. Thereby, it is particularly advantageous that the mechanical interactions in the simplified design of the bearing of the movable frames are also compensated.

In order to ensure a preferably trouble-free operation of the deflection mirror unit, operation is advantageous either above or below the mechanical resonance frequency, even though the control also allows for operation in the resonance frequency range. The mechanical resonance frequency for a typical deflection mirror lies, e.g., in the area of 5 to 50 Hz.

The control of the air-coned coils or the plunger coils for the realization of the scan pattern transmitted from the pattern generation is, according to the invention, effected digitally, for example, through pulse width modulation. This has the advantage of a simple, cost-effective and quick control. Furthermore, no heat is produced with this type of control, as would be the case, e.g., with an analog control using a variable resistor.

The actual positions of the deflection mirror of the deflection mirror unit are detected via a position sensor, which determines the displacement of the deflection mirror with regard to both rotation axes. These measurements are the input values for the control circuit and are utilized for the active control of the displacement positions with regard to achieving a preset scan pattern and for damping of unwanted interferences. Thereby, the rotation axes must not necessarily correspond to the displacement directions if suitable signal transformation is provided.

As such, the control circuit is required not so much for obtaining a certain form of movement but for damping of internal and external interferences.

According to embodiments of the invention, an optical, position-selective two-dimensional sensor, onto which the light from an additional light source is mapped for position detection via the deflection mirror, is used as position sensor for the detection of the actual positions of the deflection mirror. Contrary to a two-dimensional sensor, the light from the additional light source can alternatively be split by means of a beam splitter and detected by means of two one-dimensional sensors. Hereby, the one-dimensional sensors must be designed in such a way that the deflection not to be measured by the respective sensor does not cause an interference of the measurement. The sensors can either be designed sufficiently wide, or a focusing cylindrical lens along the sensor can be used in order to compensate interfering deflections. Instead of the aforementioned beam splitting, several additional light sources can also be applied in order to illuminate the one-dimensional sensors. In principle, a portion of the light from the light beam used for the measuring and therapy task can be separated and deflected to one or several position sensors in order to determine the deflection of the deflection The light source for position detection may be an LED, which emits a light beam with low divergence. In addition, the beam diameter can be limited through positioning a filter and/or a pinhole in front of the light source for the position detection. Hereby, it has to be taken into account that broadband laser diodes or LED's exhibit a slight tendency for producing speckles. In principle, all predominantly targeted radiating sources, such as semiconductor laser diodes or superluminescent diodes (SLD's) are suited as light source for the position detection. For the adjustment of the divergence, lenses, curved mirrors or diffractive elements can also be used.

For example, the sensor S5991-01, distributed by Hamamatsu Photonics, K.K. with headquarters in Hamamatsu City, Japan, can be used as position-sensitive optical position sensor. Hereby, the optical position sensor operates in accordance with the intensity focus principle.

For the measurement or therapy task to be solved, a two-dimensional sensor is preferred, which is available in different variations.

Even though a so-called duolateral sensor provides two differential signals, which correspond directly with both deflection directions, it is very expensive and relatively slow. Tetralateral sensors, which exhibit the same signal configuration, are significantly faster and operate with lower dark current.

A further variation are the "improved tetralateral" sensors (pincushion type). With this type of sensor, cushion effects, which occur through the mapping of a curved image plane onto a plane sensor surface, can be compensated. However, these sensors exhibit the signal outputs on the corners, so that the rotation axes are twisted by 45° with respect to the chip geometry. This increases the mathematical effort during reconstruction of the deflection values; however, these sensors operate very accurately.

In order to minimize scattered light influences, a plane-convex lens and/or a neutral density filer or an aperture with beam trap is positioned, according to the invention, before the optical position sensor.

During the detection of the actual positions of the deflection mirror, unwanted back reflections can fall onto the position sensor and distort the measurement signal.

With the use of an aperture with beam trap positioned in front of the position sensor, a large part of the unwanted scattered light can be intercepted and, therefore, not reach the sensor surface.

A neutral density filter positioned in front of the position sensor can weaken the scattered light before impinging on the sensor surface and therefore minimize its influence.

Furthermore, it is advantageous to position a plane-convex lens, the focal point of which lies on the mirror plane of the deflection mirror, in front of the position sensor. As a result, the focal beams from the deflection mirror are mapped as parallel beams on the sensor surface. This allows for an increase of the distance between the position sensor and the deflection mirror without loss regarding signal level and a further decrease of the influence of stray light.

In a first advantageous embodiment for the detection of the actual positions of the deflection mirror, the optical position sensor and the additional light source for the position detection are arranged in such a way that the light beam falls laterally to the light beam of the light source for the realization of the measurement and therapy tasks onto the deflection mirror. Due to this clear separation of the two illumination beams, their interaction can be further diminished.

After the detection of the actual positions of the deflection mirror by the position sensor, the angle determination takes place through (inverse) triangulation of the measurements.

Starting from the reflection of a light beam from an object, the position of which is to be detected in the necessary dimensions, the deflected light beam is mapped via the deflection mirror on the position-selective sensor and laterally moved on its sensor surface. Therefore, with the knowledge of the constructive relationships, the position (angle and/or distance) of the object to be measured can be deducted.

The interaction can be further diminished through an additional advantageous embodiment, whereby the light beam for the position detection and the light beam for the realization of the measurement and therapy tasks exhibit different wavelengths and appropriate spectral filters are utilized for letting pass desired portions of the radiation and for blocking undesired ones. For example, the light beam for position detection could exhibit a wavelength from the range 350 to 780 nm, preferably, 635 nm in order to realize high signals on a silicon-based position-sensitive detector. For the ophthalmological diagnosis or therapy device, however, targeted radiation with a wavelength from the range 150 nm to 1.5 µm, preferably 1 µm, is used, the crosstalk of which to the position-sensitive detector can be efficiently suppressed, e.g., through the use of a color filter in front of the detector.

In principle, a polarization separation but also a quick switchover (multiplexing) is possible for the separation of the portions of the radiation. Said options, however, are costlier to realize.

However, the separation of the portions of the radiation can also be achieved via a wavelength-selective or polarization-selective filter, which is arranged before the position sensor and which exhibits a lower transmission for the light beam for the realization of the measurement or therapy tasks than for the light beam for position detection.

If the light beam for position detection and the light beam for the realization of the measurement or therapy tasks fall from different directions onto the same spot of the deflection mirror, the detection of the actual positions of the deflection mirror is simplified due to the simpler constructive relationships. Hereby, the incidence of the two light beams from orthogonal directions represents the simplest constructive solution for the angle determination through triangulation.

For the solution of the task at hand, it also had to be taken into consideration that the sensitive optical deflection unit must be protected against damage when it is switched off and, particularly, during transport. Thereto, the intake of mechanical energy, for example, occurring resonance due to external vibrations, should be avoided, otherwise, damage to the deflection mirror unit might occur.

Numerous technical solutions seem possible for the damping of the movements of the movable frames, two variations follow.

Thereto, devices for damping of the movements of the movable frames when not in use are provided in the housing of the deflection mirror unit.

In a first embodiment thereto, the electromagnets, which function as drives according to an embodiment of the invention, for the damping of movements of the movable frames are utilized in such a way that they are short-circuited when not in use and therefore act as an electrodynamic brake.

Such shorting of the electromagnets can be activated, e.g., through drop-out of a relay when the optical deflection unit is turned off, or also by means of so-called self-conducting field-effect transistors (FET, depletion type) which become electrically conducting when currentless.

A second embodiment exhibits an additional electromagnetically activated spring element for the damping of movements of the movable frames, which presses the movable frames against the housing when not in use. During operating conditions, said spring element could, e.g., be pulled away from the frame by means of an electromagnet.

With the arrangement, according to the invention, an optical deflection unit for ophthalmological devices is provided which is particularly suited for biometric measurement tasks. The optical deflection unit and, particularly its deflection mirror unit, are significantly more cost-efficient and less elaborate and are characterized by simplicity, durability, and robustness.

Hereby, the cardan suspension allows for an ideal or largely decoupled control of the two motion axes and the positioning of the rotation axes in the mirror surface plane. This is particularly advantageous in order to generally minimize motion components of the mirror surface in the direction of the radiation dispersal when an ophthalmological diagnosis device, based on interferometry, is used.

Thereto, the flexural pivots and/or the pretensioned hybrid ball bearings allow for lubrication-free rotation, free of play and wear and tear.

Aside from the already mentioned advantages of a lubrication-free, compact deflection mirror unit, free of play and wear and tear, the optical deflection unit, according to embodiments of the invention, may be characterized by the following features:

Simple control
High reproducibility of the deflections
Little wear and tear
High temperature stability
High durability of the scanner
Realization of large deflections
Compact design
Small number of optical elements
Absolute or relative position detection
Simple control circuits for the compensation of interferences
Possible one- and two-dimensional measurements and
Capability of large mirror dimensions of up to ½ inch.

Although the description above contains many specificities, these should not be construed as limiting the scope of the invention but merely as providing illustrations of some of the presently preferred embodiments of the invention. Thus, the scope of the invention should be determined by the appended claims and their legal equivalents, rather than by the examples given.

We claim:

1. An optical deflection unit for scanning, ophthalmological measuring, and therapy systems comprising:
    a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
    a position sensor; and
    a control unit;
    the deflection mirror, the position sensor, and the control unit forming a control circuit for minimizing deviation of actual positions, detected by the position sensor, from the desired positions of the deflection mirror;
    wherein the deflection unit comprises a housing with a movable frame movable in an oscillating fashion around the at least one rotation axis, the frame holding the deflection mirror, and being secured in the housing via two bearings and the frame having permanent magnets, and wherein the deflection unit further includes, in the housing, non-contacting, electromagnetic drives in the form of electromagnets, which face the permanent magnets; and
    wherein the frame, which is movable in an oscillating fashion around a rotation axis in the housing, is further pivoted around an additional rotation axis, and wherein the two rotation axes lie orthogonally to one another.

2. The optical deflection unit, according to claim 1, wherein electromagnets in the form of air cored coils or plunger coils are used as non-contacting electromagnetic drives.

3. The optical deflection unit, according to claim 1, wherein the movable frame, which holds the deflection mirror, is secured in the housing in such a way that the at least one rotation axis lies in the mirror plane.

4. The optical deflection unit, according to claim 1, wherein at least one of lubrication-free flexural pivots and pretensioned hybrid ball bearings are used as bearings for the movable frame.

5. An optical deflection unit for scanning, ophthalmological measuring, and therapy systems comprising:
    a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
    a position sensor; and
    a control unit;
    the deflection mirror, the position sensor, and the control unit forming a control circuit for minimizing deviation of actual positions, detected by the position sensor, from the desired positions of the deflection mirror;
    wherein the deflection unit comprises a housing with two movable frames including an inner movable frame and an outer movable frame, wherein the inner movable frame holds the deflection mirror, includes permanent magnets, and is secured via two bearings in the outer movable frame, which also includes permanent magnets and is secured via two bearings in the housing, and wherein the deflection unit includes in the housing non-contacting, electromagnetic drives in the form of electromagnets, which face the permanent magnets.

6. The optical deflection unit, according to claim 5, wherein the movable frames as well as the arrangement of the permanent magnets are symmetrical to the rotation axes.

7. The optical deflection unit, according to claim 6, wherein the permanent magnets are arranged in pairs on the rotation axis.

8. The optical deflection unit, according to claim 5, wherein the housing of the deflection unit further comprises devices for damping the movements of the movable frames when not in use.

9. The optical deflection unit, according to claim 5, wherein the electromagnets, functioning as non-contacting, electromagnetic drives, are used for damping of the movement of the movable frames, and wherein the electromagnets are short-circuited when not in use and act as an electrodynamic brake.

10. The optical deflection unit, according to claim 5, further comprising an additional electromagnetically activated spring element that is used for damping of the movement of the movable frames and which secures the movable frames when not in use.

11. An optical deflection unit for scanning, ophthalmological measuring, and therapy systems comprising:
a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
a position sensor; and
a control unit;
the deflection mirror, the position sensor, and the control unit forming a control circuit for minimizing deviation of actual positions, detected by the position sensor, from the desired positions of the deflection mirror;
wherein the deflection unit comprises a housing with two movable frames including an inner movable frame and an outer movable frame, wherein the inner movable frame holds the deflection mirror, includes permanent magnets, for both rotation axes and is secured via two bearings in the outer movable frame, which, in turn, is secured via two bearings in the housing, and wherein the deflection unit includes, in the housing, non-contacting, electromagnetic drives in the form of electromagnets, which face the permanent magnets.

12. The optical deflection unit, according to claim 11, wherein the permanent magnets are arranged in pairs.

13. An optical deflection unit for scanning, ophthalmological measuring, and therapy systems comprising:
a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
a position sensor; and
a control unit;
the deflection mirror, the position sensor, and the control unit forming a control circuit for minimizing deviation of actual positions, detected by the position sensor, from the desired positions of the deflection mirror;
wherein the deflection unit comprises a housing with a movable frame, movable in an oscillating fashion around the at least one rotation axis, the frame holding the deflection mirror, and being secured in the housing via two bearings and the frame having permanent magnets, and wherein the deflection unit further includes, in the housing, non-contacting, electromagnetic drives in the form of electromagnets, which face the permanent magnets; and
wherein the deflection mirror is detachably connected with the movable frame.

14. An optical deflection unit for scanning, ophthalmological measuring, and therapy systems comprising:
a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
a position sensor; and
a control unit;
the deflection mirror, the position sensor, and the control unit forming a control circuit for minimizing deviation of actual positions, detected by the position sensor, from the desired positions of the deflection mirror;
wherein control of the non-contacting, electromagnetic drives in the form of electromagnets is effected digitally for the realization of the scan pattern transmitted by pattern generation.

15. The optical deflection unit, according to claim 14, wherein the control of the non-contacting, electromagnetic drives in the form of electromagnets is affected through pulse modulation.

16. An optical deflection unit for scanning, ophthalmological measuring, and therapy systems comprising:
a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
a position sensor; and
a control unit;
the deflection mirror, the position sensor, and the control unit forming a control circuit for minimizing deviation of actual positions, detected by the position sensor, from the desired positions of the deflection mirror;
wherein an optical, position-selective, two-dimensional sensor is used as position sensor for the detection of the actual positions of the deflection mirror and upon which light of an additional light source is mapped for position detection via the deflection mirror.

17. An optical deflection unit for scanning, ophthalmological measuring, and therapy systems comprising:
a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
a position sensor; and
a control unit;
the deflection mirror, the position sensor, and the control unit forming a control circuit for minimizing deviation of actual positions, detected by the position sensor, from the desired positions of the deflection mirror;

wherein the position sensor comprises an optical position sensor and operates in accordance with the intensity focus principle.

18. The optical deflection unit, according to claim 17, wherein the optical position sensor and an additional light source for position detection are arranged in such a way that a second light beam falls onto the deflection mirror laterally to a first light beam of a first light source for the realization of the measurement and therapy tasks.

19. The optical deflection unit, according to claim 18, wherein the light beam for position detection and the light beam for the realization of the measurement and therapy tasks exhibit different wavelengths or polarization states or fall from different directions onto the same spot on the deflection mirror.

20. The optical deflection unit, according to claim 19, wherein a wavelength-selective or polarization-selective filter is positioned before the optical position sensor and which exhibits a lower transmission for the light beam for the realization of the measurement and therapy tasks than for the light beam for position detection.

21. The optical deflection unit, according to claim 18, wherein the light beam for position detection and the light beam for the realization of the measurement and therapy tasks fall from orthogonal directions onto the same spot on the deflection mirror.

22. The optical deflection unit, according to claim 18, wherein an LED, which radiates a light beam of low divergence, is used as light source for position detection.

23. The optical deflection unit, according to claim 18, wherein a filter and/or a pinhole is positioned in front of the light source for position detection.

24. An optical deflection unit for scanning, ophthalmological measuring, and therapy systems comprising:
   a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
   a position sensor; and
   a control unit;
   the deflection mirror, the position sensor, and the control unit forming a control circuit for minimizing deviation of actual positions, detected by the position sensor, from the desired positions of the deflection mirror;
   further comprising a plano-convex lens, a neutral density filter, an aperture with beam trap for minimizing scattered light influences, or a combination thereof is positioned before the optical position sensor.

25. An optical deflection unit for scanning, ophthalmological measuring, and therapy systems comprising:
   a deflection mirror, movable through non-contacting electromagnetic drives in an oscillating fashion around at least one rotation axis, and the deflection mirror being arranged between at least two bearings in the direction of the at least one rotation axis, and the at least one rotation axis lying within a plane of the deflection mirror;
   a position sensor; and
   a control unit;
   the deflection mirror, the position sensor, and the control unit forming a control circuit for minimizing deviation of actual positions, detected by the position sensor, from the desired positions of the deflection mirror;
   wherein the deflection unit comprises a housing with a movable frame, movable in an oscillating fashion around the at least one rotation axis, the frame holding the deflection mirror, and being secured in the housing via two bearings and the frame having permanent magnets, and wherein the deflection unit further includes, in the housing, non-contacting, electromagnetic drives in the form of electromagnets, which face the permanent magnets;
   wherein the electromagnets, functioning as non-contacting, electromagnetic drives, are used for damping of the movement of the movable frame, and wherein they are short-circuited when not in use and act as an electrodynamic brake.

* * * * *

UNITED STATES PATENT AND TRADEMARK OFFICE
CERTIFICATE OF CORRECTION

PATENT NO. : 8,736,935 B2
APPLICATION NO. : 12/886145
DATED : May 27, 2014
INVENTOR(S) : Gerard Antkowiak et al.

Page 1 of 1

It is certified that error appears in the above-identified patent and that said Letters Patent is hereby corrected as shown below:

In the Specification

Col. 4, please delete lines 58-62.

"FIG. 3*b* is a side schematic view of the deflection unit, according to FIG. 3*a*, with electromagnets in the form of air-cored coils; and
FIG. 3*c* is a side view of the deflection unit, according to FIG. 3*a*, with electromagnets in the form of plunger coils.".

Signed and Sealed this
Nineteenth Day of August, 2014

Michelle K. Lee
*Deputy Director of the United States Patent and Trademark Office*